United States Patent [19]

Frank

[11] 4,310,522

[45] * Jan. 12, 1982

[54] CHICKEN FEED COMPOSITION

[75] Inventor: Fred R. Frank, Kalamazoo, Mich.

[73] Assignee: The Upjohn Company, Kalamazoo, Mich.

[*] Notice: The portion of the term of this patent subsequent to Jul. 9, 1991, has been disclaimed.

[21] Appl. No.: 138,612

[22] Filed: Apr. 9, 1980

Related U.S. Application Data

[63] Continuation of Ser. No. 731,814, Oct. 12, 1976, abandoned, which is a continuation of Ser. No. 592,821, Jul. 3, 1975, Pat. No. 4,012,509, which is a continuation of Ser. No. 477,765, Jun. 10, 1974, abandoned, which is a continuation-in-part of Ser. No. 218,480, Jan. 17, 1972, Pat. No. 3,823,237, which is a continuation-in-part of Ser. No. 210,232, Dec. 20, 1971, abandoned.

[51] Int. Cl.$^3$ .............................................. A61K 31/59
[52] U.S. Cl. .................................................... 424/236
[58] Field of Search ........................................ 424/236

[56] References Cited

U.S. PATENT DOCUMENTS 3,639,596  2/1972  De Luca et al. .................... 424/236
3,646,203  2/1976  De Luca et al. .................... 424/236

Primary Examiner—Frederick E. Waddell
Attorney, Agent, or Firm—Martin B. Barancik; William J. Scanlon

[57] ABSTRACT

The administration of 25-hydroxycholecalciferol, 24,25-dihydroxycholecalciferol, 25,26-dihydroxycholecalciferol, 1,25-dihydroxycholecalciferol, 25-hydroxydihydrotachysterol$_3$, 25-hydroxyergocalciferol, 1-α-hydroxycholecalciferol, and their acylates to hens increases the thickness of the egg shells. Compositions and methods are provided.

7 Claims, No Drawings

CHICKEN FEED COMPOSITION

CROSS REFERENCE TO RELATED APPLICATIONS

This is a continuation of application Ser. No. 731,814, filed Oct. 12, 1976, now abandoned, which is a continuation of application Ser. No. 592,821, filed July 3, 1975, now issued as U.S. Pat. No. 4,012,509, which is a continuation of Ser. No. 477,765, filed June 10, 1974, which is now abandoned, which is a continuation-in-part application of Ser. No. 218,480, filed Jan. 17, 1972, and now issued as U.S. Pat. No. 3,823,237, which is a continuation-in-part of application Ser. No. 210,232, filed Dec. 20, 1971 and now abandoned.

THE BACKGROUND

The poultry industry has recently made significant advances in dealing with many of its problems! However, one problem area which has met with little success is the effort to decrease the incidence of broken hens' eggs. Approximately 5-8% of eggs laid by hens are prematurely broken with a loss to egg producers of up to $100 million dollars or more per year. Generally, the reason for the premature breakage appears to be insufficient calcification of the egg shell, a condition which produces an egg shell which is too thin to withstand forces exerted upon it. It is well known that Vitamin $D_3$ affects the shell thickness of hens' eggs. However, Vitamin $D_3$ has little or no effect on the thickness of egg shells from some hens. Furthermore, the activity of Vitamin $D_3$ for increasing shell thickness reaches a plateau which does not show an increase even at extremely high dosages of Vitamin $D_3$.

Recently an active metabolite of Vitamin $D_3$ has been isolated. This metabolite, the 25-hydroxy derivative of Vitamin $D_3$, generically known as 25-hydroxycholecalciferol, and referred to hereafter as 25-HCC, has been shown to be more active than Vitamin $D_3$ in the rat line rickets cure assay and in the rickets prevention assay in young chicks.

However, no particular tests using 25-HCC in mature egg-laying chickens or other species are disclosed in the prior art. Perhaps of even greater significance, only problems dealing with bone calcification such as rickets and osteomalacia, or general membrane calcium transport, such as cattle milk fever and hypoparathyroidism in humans have been dealt with by the art.

The increasing of hen egg shell thickness and the curing or preventing of bone conditions such as rickets and osteomalacia proceed by different physiological mechanisms of action. The substrate which is responsible for increasing shell thickness is calcium carbonate. The substance deposited which aids in treating the various bone diseases is calcium hydroxyapatite, a complex mineral-like salt of phosphorus, oxygen, and calcium which is chemically unrelated to carbonate. Furthermore, the organic matrices in which each of these substances is deposited differ radically from each other. Egg shell organic matrix is comprised of noncellular amorphous sheets of protein. The bone organic matrix is formed, living tissue capable of reproducing itself.

BRIEF SUMMARY OF THE INVENTION

It has been found that 25-HCC and related compounds to be described hereinafter have the capacity to increase the thickness of hens' egg shells. When administered to hens, these compounds increase the thickness of shells from a substantial number of hens whose egg shells exhibit a thickness of less than or equal to 0.013 inch, a thickness which is considered to be critical since most breakage occurs in egg shells with a thickness less than 0.013 inch.

Therefore, in accordance with this invention, a feed formulation for increasing the thickness of hens' egg shells is disclosed comprising a chicken feed in combination with an egg shell thickening effective but non-toxic quantity of a compound selected from the group consisting of

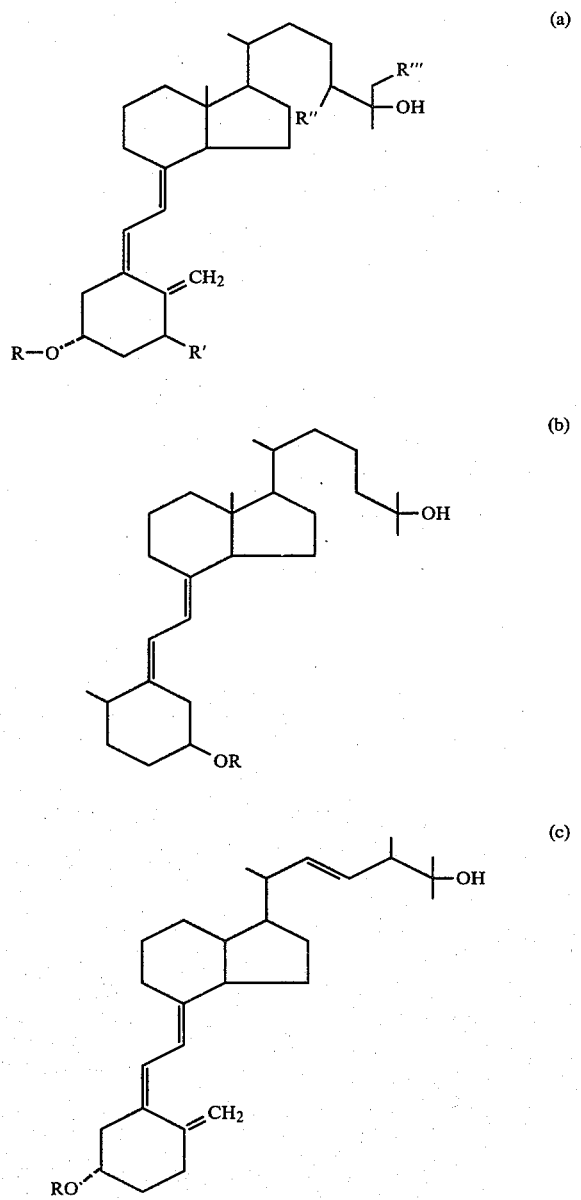

and

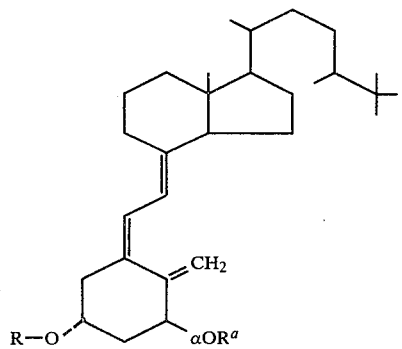

(d)

where R=H, or acyl where acyl is an acyl radical of normal or isomerized alkane carboxylic acid of from 2 to about 8 carbon atoms and R', R", and R'" can be H, OH, or O acyl wherein acyl is defined as above, but that at least two of R', R", and R'" must be hydrogen and that if R', R", or R'" is OH then R must be H, and if R', R", or R'" is O acyl, acyl defined as above, then R must be the same acyl, and $R^a$ is selected from hydrogen or acyl as defined above and when $R^a$ is hydrogen, R is hydrogen and when $R^a$ is acyl, R is the same acyl.

A further aspect of this invention is the process for increasing the shell thickness of eggs from hens comprising feeding the hens an egg shell thickening chicken feed which comprises a chicken feed in combination with an egg shell thickening effective but non-toxic quantity of a compound selected from the group of compounds disclosed above with reference to composition components except that 25 hydroxy cholecalciferol and its acylates are omitted.

DETAILED DESCRIPTION OF THE INVENTION

The compounds employed in the compositions and uses of those compositions are prepared by methods known to the art. The unacylated compounds of the invention have been prepared in the following references:

Formula A

25-HCC—R=R'=R"=R'"=H  U.S. Pat. No. 3,565,924
24,25—Dihydroxycholecalciferol—R=R'=R'"=H, R"=OH U.S. Pat. No. 3,715,374
25,26—Dihydroxycholecalciferol—R=R'=R"=H, R'"=OH Biochemistry 9:24:4776–4780, 1970
1α, 25—Dihydroxycholecalciferol—R=R"=R'"=H, R'=OH Biochemistry 10:14:2799–2804, 1971

Formula B

25—Hydroxydihydrotachysterol₃-R=H  Federation Proceedings 29:2:687, 1970

Formula C

25—Hydroxyergocalciferol, R=H, Biochemistry 8:9:3515–3519, 1969

Formula D

1α—Hydroxycholecalciferol, R=H J. Am. Chem. Soc. 95:8, 2748 (1973).

The acylated compounds of this invention can be prepared by taking any of the above unacylated compounds and reacting it with the acid anhydride or chloride of the two to eight carbon atom hydrocarbon carboxylic acid desired according to the method disclosed in Example 16 of Babcock and Campbell, Belgian Pat. No. 747,492. Illustrated reactants and respective products are the following:

25-hydroxycholecalciferol treated with acetic anhydride gives 25-hydroxycholecalciferol 3-acetate
25-hydroxycholecalciferol treated with butyryl chloride gives 25-hydroxycholecalciferol 3-butyrate
25-hydroxycholecalciferol treated with octanoyl chloride gives 25-hydroxycholecalciferol 3-octanoate
24,25-dihydroxycholecalciferol treated with acetic anhydride gives 24,25-dihydroxycholecalciferol 3,24-diacetate
24,25-dihydroxycholecalciferol treated with isobutyryl chloride gives 24,25-dihydroxycholecalciferol 3,24-diisobutyrate
25,26-dihydroxycholecalciferol treated with propionic anhydride gives 25,26-dihydroxycholecalciferol 3,26-dipropionate
1α, 25-dihydroxycholecalciferol treated with pentanoic anhydride gives 1,25-dihydroxycholecalciferol 1,3-dipentanoate
25-hydroxydihydrotachysterol₃ treated with acetic anhydride gives 25-hydroxydihydrotachysterol 3-acetate
25-hydroxyergocalciferol treated with acetic anhydride gives 25-hydroxyergocalciferol-3-acetate
1α-hydroxycholecalciferol treated with propionyl chloride gives cholecalciferol 1,3-dipropinate It is preferred to use the hydrated forms of the metabolites whenever possible. For example, the hydrate of 25-HCC is preferred over the non-hydrate of 25-HCC. The method of preparation is disclosed in Belgian Pat. No. 747,492, Example 8.

The chicken feed into which the compounds are combined is any standard diet fed an egg-laying hen. An example of such a diet is given below:

| Ingredients | Layer Formulation (Fed after 20 weeks of age) (Pounds) |
| --- | --- |
| Corn meal, No. 2 yellow, ground | 667.5 |
| Soybean meal 50% protein | 100 |
| Fish meal 65% protein | 15 |
| Meat and bone scraps 50% protein | 75 |
| Corn distillers dried solubles | 50 |
| Alfalfa meal 17% protein | 15 |
| Limestone, ground | 70 |
| Salt, iodized | 2.5 |
| DL-Methionine | 0.5 |
| Vitamin premix | 5 |
| Calculated Composition | |
| Protein, % | 17.2 |
| Calcium, % | 3.4 |

The calcium level for egg-laying hens is well known and important for the calcification of egg shells. Generally from about 2.5 to about 5.5% calcium, calculated as weight of calcium per weight of feed formulation is required, preferably from about 3.0 to about 4.0%. When levels of calcium at the upper end of the range are employed, a diet with increased energy and protein concentration can be used.

Prior to combination of the active compound with the feed, it is preferable to coat the compound to prevent degradation. This is particularly desirable when employing the non-hydrated form of the compound. Any of the standard vitamin coatings can be employed. For example, the crystalline compound can be coated with a solid antioxidant in an amount sufficient only to coat the surface of the crystals with the substance and then drying the crystals as in U.S. Pat. No. 3,110,783, or a solid or liquid composition containing the compounds can be stabilized by addition of standard antioxidants such as a tocopherol, propyl gallate, butylated hydroxy anisole, and butylated hydroxy toluene.

The active compound can be combined with the chicken feed formulation as the pure compound or in combination with other feed components, in its crystalline form, in solution, or in suspension, as long as the compound is uniformly present throughout the feed compositions.

The compound should be present in the feed formulation in egg shell thickening but non-toxic quantities. As much compound can be used as desired as long as toxic effects are not observed. The preferred quantity of compound is that minimum amount which induces the desired egg shell thickening results. Quantities of 25-HCC of from about 5 μg to about 20 μg./lb. of feed formulation have induced egg shell thickening results as shown in Example 1.

The feed formulation of this invention is fed to hens on a normal dietary intake and desired egg shell thickening is observed.

The following examples are illustrative of the invention and are not to be construed as limiting the invention.

EXAMPLE 1

150 Hyline strain SCWL hens fed with a diet including a commercially available form of stabilized Vitamin $D_3$ and producing eggs with shells varying in thickness from less than 0.011 to greater than 0.015 inch, are evenly distributed amoung six treatment groups so that each treatment group contained all representative values of shell thickness. To a basal non-Vitamin-D supplemented feed formulation is added daily either 25-HCC or Vitamin $D_3$. This diet is then fed to hens. The daily formulation was done to avoid vitamin degradation. Shell changes and rate of production are determined weekly. The chickens are on this schedule for ten weeks.

The results from this experiment show that shell thicknesses increased after administration of 25-HCC or Vitamin $D_3$ from 0.001 to 0.003 inch. The increase in shell thickness of eggs from hens treated with 25-HCC was at least as good as from hens treated with Vitamin $D_3$. Egg production appears to be unchanged after treatment with 25-HCC.

Tables I and II present data with regard to improving shell thickness in eggs from a given number of hens after administration of 25-HCC or Vitamin $D_3$.

TABLE I

COMPARISON OF VIT $D_3$ AND 25-HCC EFFECTS ON HENS LAYING EGGS <0.013 INCH THICK

| Chicken Group | Compound | μg./lb. of Feed | Formulation | Number Hens Producing Shells <0.013 Inch Thick | Number Hens With Improved Shell Calcification | % of Hens with Shell Improvement |
|---|---|---|---|---|---|---|
| 1 | Vitamin $D_3$ | 10 | Crystalline | 16 | 6/16 | 37.5% |
| 2 | Vitamin $D_3$ | 10 | Propylene Glycol | 14 | 6/14 | 42.8% |
| 3 | 25-HCC | 5 | Propylene Glycol | 12 | 9/12 | 75.0% |
| 4 | 25-HCC | 10 | Propylene Glycol | 11 | 8/11 | 72.7% |
| 5 | 25-HCC | 10 | Crystalline | 15 | 13/15 | 86.6% |
| 6 | 25-HCC | 20 | Propylene Glycol | 11 | 9/11 | 81.8% |

TABLE II

COMPARISON OF VIT $D_3$ AND 25-HCC EFFECTS ON HENS LAYING EGGS >0.013 INCH THICK

| Chicken Group | Compound | μg./lb. of Feed | Formulation | Number Hens Producing Shells >0.013 Inch Thick | Number Hens With Improved Shell Calcification | % of Hens With Shell Improvement |
|---|---|---|---|---|---|---|
| 1 | Vitamin $D_3$ | 10 | Crystalline | 6 | 1/6 | 17.0% |
| 2 | Vitamin $D_3$ | 10 | Propylene Glycol | 9 | 2/9 | 22.0% |
| 3 | 25-HCC | 5 | Propylene Glycol | 7 | 4/7 | 56.5% |
| 4 | 25-HCC | 10 | Crystalline | 7 | 4/7 | 56.5% |
| 5 | 25-HCC | 10 | Propylene Glycol | 6 | 3/6 | 50.0% |
| 6 | 25-HCC | 20 | Propylene Glycol | 8 | 5/8 | 62.5% |

The results of Tables I and II clearly demonstrate the surprising superiority of 25-HCC over Vitamin $D_3$ with regard to improving shell thickness in eggs from a given number of hens. Where the egg shells are initially less than 0.013 inch, which may indicate an insufficient utilization of Vitamin $D_3$ by the hen, the number of hens whose egg shell thicknesses increased with administration of 25-HCC was double that of the hens treated with Vitamin $D_3$. Moreover, the dosages of 10 and 20 μg. are on the Vitamin $D_3$ activity plateau previously noted. Where the egg shells are initially greater than 0.013 inch, the improvement of shell thickness when using 25-HCC is even more pronounced. The number of hens whose shell thickness increased after administration of 25-HCC was approximately two and a half that of the hens treated with Vitamin $D_3$. Since these were seemingly normal hens, the results cannot be explained by any theory now known.

Although 5 μg. of 25-HCC was the smallest quantity employed in this experiment, this does not imply that desired egg shell thickening results cannot be achieved with smaller quantities. Likewise quantities above 20 μg. could be equally or perhaps even more effective without showing observable toxic effects.

EXAMPLE 2

A calcium source such as oyster shells, physically separated from the chicken feed formulation, and impregnated with sufficient 25-HCC to provide 3 μg. of 25-HCC per chicken per day is fed to chickens. The chickens ingest the oyster shell and absorb the 25-HCC from the digestive tract. Desired egg shell thickening is observed in subsequently laid eggs.

Examples 3 and 4 illustrate additional methods of administering the active compound to egg laying hens.

EXAMPLE 3

A quantity of 25-HCC sufficient to administer to a chicken about 3 μg. of 25-HCC per day, assuming average water intake per day of the chicken, is metered into the chicken's water supply. To facilitate proper dispersion, the 25-HCC can be micronized if desired and dissolved in a surfactant such as polysorbate 80, and metered into the water supply. The chickens ingest their normal quantity of water including the 25-HCC. Desired egg shell thickening is observed in subsequently laid eggs.

EXAMPLE 4

A quantity of 25-HCC sufficient to provide a chicken with 60 days supply of 25-HCC is combined with an inert carrier such as a mineral oil and injected subcutaneously into the web of the wing. The 25-HCC is slowly released and absorbed. Desired egg shell thickening is observed in subsequently laid eggs.

EXAMPLE 5

In a similar manner as exemplified in Examples 1, 2, 3, and 4, 24,25-dihydroxycholecalciferol, 25,26-dihydroxycholecalciferol, 25-hydroxyergocalciferol, 25-hydroxydihydrotachysterol$_3$, 1α,25-dihydroxycholecalciferol, and 1α-hydroxycholecalciferol are administered to egg laying hens and results similar to those of Examples 1, 2, 3, and 4 are obtained.

EXAMPLE 6

In a similar manner as exemplified in Examples 1, 2, 3, and 4, 25-hydroxycholecalciferol 3-acetate, 25-hydroxycholecaliferol 3-butyrate, 25-hydroxycholecalciferol 3-octanoate, 24,25-dihydroxycholecalciferol 3,24-diacetate, 24,25-dihydroxycholecalciferol 3,24-diisobutyrate, 25,26-dihydroxycholcalciferol 3,26-dipropionate, 1α, 25-dihydroxycholecalciferol 1,3-dipentanoate, 25-hydroxydihydrotachysterol$_3$ 3-acetate, 25-hydroxyergocalciferol 3-acetate, and 1α-cholecalciferol-1,3-dipropionate are administered to egg-laying hens and results similar to those of Examples 1, 2, 3, and 4 are obtained.

It should be noted that the parent molecules of the hydroxylated dihydrotachysterol and ergocalciferol metabolites are not known for their egg shell thickening abilities. Consequently, any egg shell thickening effects should be unexpected in their particular cases.

When employing an acylate the dosage should be related to its unacylated parent molecule on a molar basis. For example, approximately 1.6 μg. of 24,25-dihydroxycholecalciferol 3,24-dioctanoate is equivalent to 1.0 μg. 24,25-dihydroxycholecalciferol.

I claim:

1. A chicken feed composition for egg-laying hens comprising, in combination with a chicken feed, an effective but non-toxic egg shell thickening amount of a compound selected from the group consisting of:

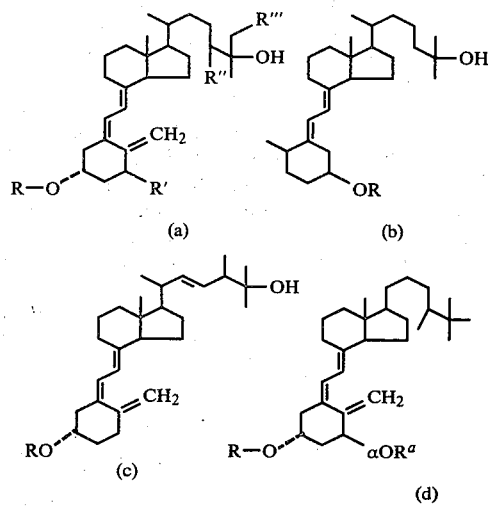

where R=H, or acyl where acyl is an acyl radical of normal or isomerized alkane carboxylic acid of from 2 to about 8 carbon atoms, inclusive, and R', R", and R''' is H, OH, or acyl wherein acyl is defined as above, but that at least two of R', R", and R''' must be hydrogen and that if R', R", or R''' is OH, then R must be H, if R', R", or R''' is O acyl, acyl defined as above, then R must be the same acyl, and $R^a$ is selected from hydrogen or acyl as defined above and when $R^a$ is hydrogen, R is hydrogen and when $R^a$ is acyl, R is the same acyl, said chicken feed composition having from about 2.5 to about 5.5% calcium by weight.

2. The composition of claim 1 wherein there is from about 5 μg. to about 20 μg. of the compound per pound of feed.

3. The composition of claim 1 wherein the compound is selected from the group consisting of 25-hydroxycholecalciferol; 24,25-dihydroxycholecalciferol; 25,26-dihydroxycholecalciferol; 1α, 25-dihydroxycholecalciferol; 25-hydroxydihydrotachysterol$_3$; 25-hydroxyergocalciferol and 1α-hydroxycholecalciferol.

4. The composition of claim 3 wherein the compound is 25-hydroxycholecalciferol.

5. The composition of claim 3 wherein the compound is 1α-hydroxycholecalciferol.

6. The composition of claim 3 wherein the compound is selected from the group consisting of 25-hydroxyergocalciferol and 25-hydroxydihydrotachysterol$_3$.

7. The composition of claim 4 wherein the 25-hydroxycholecalciferol is present in quantities of about 5 μg. to about 20 μg.

* * * * *